US00PP20700P2

(12) United States Plant Patent
Kordes

(10) Patent No.: US PP20,700 P2
(45) Date of Patent: Feb. 2, 2010

(54) SHRUB ROSE PLANT NAMED 'KORSTEIMM'

(50) Latin Name: *Rosa hybrida*
Varietal Denomination: KORsteimm

(75) Inventor: Wilhelm Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/228,863

(22) Filed: Aug. 15, 2008

(51) Int. Cl.
*A01H 5/00* (2006.01)

(52) U.S. Cl. ..... Plt./104
(58) Field of Classification Search ..... Plt./104
See application file for complete search history.

(56) References Cited

FOREIGN PATENT DOCUMENTS

EM 2007/1338 6/2007

*Primary Examiner*—Annette H Para

(57) ABSTRACT

A new and distinct variety of rose with long lasting, novel yellow flowers, and attractive foliage with good disease resistance. It exhibits upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORsteimm'.

BACKGROUND OF THE INVENTION

The new variety of rose plant of the present invention originated from a controlled crossing in a breeding program of two distinct parents during the summer of 1998. The crossing was between 'TANeitber' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORsteimm'.

SUMMARY OF THE INVENTION

The new rose plant may be distinguished from its seed parent, 'TANeitber', by the following combination of characteristics:

1. 'KORsteimm' has yellow flowers, while 'TANeitber' has amber yellow flowers.
2. 'KORsteimm' has double flowers, whereas 'TANeitber' has very double flowers.
3. The disease resistance of 'KORsteimm' is very good, while disease resistance of 'TANeitber' is average.

The new rose plant may be distinguished from its pollen parent, an 'un-named seedling' by the following combination of characteristics:

1. 'KORsteimm' has yellow petals while the 'un-named seedling' has pink petals.
2. 'KORsteimm' has double flowers, while the 'un-named seedling' has semi-double flowers.

The objective of the hybridization was to create a new and distinct rose plant with unique qualities, such as:

1. Uniform growth and flowering;
2. Abundant attractive, recurrent yellow flowers;
3. Attractive and abundant foliage; and
4. Resistance to diseases encountered in landscapes and gardens.

This combination of qualities is not present in prior rose cultivars. These objectives have been substantially achieved and in that distinguish 'KORsteimm' from all other varieties of which we are aware.

As part of a rose development program, Wilhelm Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORsteimm' was selected in May, 1998 from the seedling beds to be asexually propagated for further evaluation. The first asexual propagation of 'KORsteimm' was done by budding to seedling understocks in July, 1998 at the inventor's nursery in Offenseth-Sparrieshoop, Germany.

This initial and other subsequent propagations conducted in controlled environments demonstrate that 'KORsteimm' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORsteimm'. Specifically illustrated in SHEET ONE is a stem exhibiting thorns; buds and flowers in different phases of opening; juvenile foliage with tip of stem; detached petals, dissected receptacle and detached sepal; and leaves.

DETAILED BOTANICAL DESCRIPTION

The following is a description of 'KORsteimm', as observed in its growth in August, 2008 in a greenhouse in Offenseth-Sparrieshoop, Germany on plants of two years of age. Color references are made using The Royal Horticultural Society (London, England) Colour Chart, 2001 except where common terms of color are used.

For a comparison, several physical characteristics of the rose variety 'TANeitber', are compared to 'KORsteimm' in Chart 1.

CHART 1

| Characteristic | 'KORsteimm' | 'TANeitber' |
|---|---|---|
| Petal color, upper surface | Yellow Group 11B | Yellow-Orange Group 22B |
| Petal color, lower surface | Yellow Group 11C | Yellow-Orange Group 22C |
| Petal count | 35 | 40-50 |

Parents:

*Seed parent.*—'TANeitber'.

*Pollen parent.*—An 'un-named seedling'.

Classification:

*Botanical classification.—Rosa hybrida,* 'KORsteimm'.

*Commercial classification.*—Shrub rose.

FLOWER AND FLOWER BUD

Blooming habit: Recurrent.

Flower bud:

*Size.*—Upon opening, 25 mm in length from base of receptacle to end of bud and 25 mm in diameter at its widest point.

*Bud form.*—Cupped.

*Bud color.*—As sepals first unfold, bud color is Yellow Group 7A. When ¼ open, the upper surface of petals is Yellow Group 7A, and the lower surface of petals is Yellow Group 7A.

*Sepals.*—Size: Average 7 mm long×4 mm wide. Shape: Sepal shape is narrowly ovate with an acute tip. Base is flat at union with receptacle. Quantity: Five. Margins: With stipitate glands on inner surface. Surface texture: Leathery. Color: Upper surface Green Group 144B. Lower surface Green Group 143A.

*Receptacle.*—Surface: Smooth, glabrous. Color: Green Group 144A. Shape: Campanulate. Size: 10 mm (h)×7 mm (w).

*Peduncle.*—Surface: Smooth. Length: 20 mm average length. Diameter: 1 mm average diameter. Color: Yellow-Green Group 144A. Strength: Strong. Borne: Singly. 1–3 buds per flowering stem.

Flower bloom:

*Fragrance.*—Weak.

*Duration.*—The blooms have a duration on the plant of approximately 5–6 days. Senesced petals drop away cleanly.

*Size.*—Medium flowered garden rose. When open, the average flower diameter is 80 mm and the average flower height is 40 mm.

*Form.*—Shape of flower when viewed from the side: Upon opening, upper part: Flattened convex. Upon opening, lower part: Concave. Open flower, upper part: Flat. Open flower, lower part: Concave.

Color:

*Upon opening, petals.*—Upper surface: Yellow Group 11B. Lower surface Yellow Group 11C.

*After opening, petals.*—Upper surface: Yellow Group 11B. Lower surface Yellow Group 11C. No distinctive coloration at petal base observed. Variegations: None.

General tonality: On open flower, Yellow Group 12C. No change in the general tonality at the end of the 3rd day. Afterwards, general tonality is Yellow Group 12D.

Petals:

*Petal count.*—Approximately 30–35 petals under normal conditions.

*Petal reflex.*—Petals reflex weakly.

*Petal edge.*—Uniform.

*Petal shape.*—Narrow elliptical.

*Petal size.*—42 mm long; 30 mm wide.

*Thickness.*—Average.

*Petal arrangement.*—Generally in a regular pattern with overlapping edges.

Petaloids: None observed.

Reproductive organs:

*Pistils.*—Approximately 30 present. Stigmas: Location: Inferior in position to anthers. Color: Yellow Group 11C. Styles: Length: 7 mm long. Color: Green-Yellow Group 1D.

*Stamens.*—Approximately 50 on average and regularly arranged. Anthers: Size: 2 mm long. Color: Yellow Group 12A. Pollen: Generally present. Color: Yellow Group 12A. Filaments: Color: Yellow Group 12C. Length: 10 mm.

THE PLANT

*Plant growth.*—Vigorous. Upright to bushy habit. When grown as a budded nursery plant the average plant height is 80 cm and the average plant width is 50 cm.

*Stems.*—Stem color: Young wood: Yellow-Green Group 144A. Older wood: Yellow-Green Group 144A. Stem surface: Young wood: Smooth. Older wood: Smooth.

*Prickles.*—Present. Incidence: 8–10 per 10 cm of stem. Size: Average length: 5–6 mm. Color: Greyed-Yellow Group 160A. Shape: Deep concave.

*Leaves and leaflets.*—Normally 5–7 leaflets on normal leaves in middle of the stem. Venation pattern: Pyramidal net pattern. Leaf size: 100 mm (l)×75 mm (w). Quantity: Very. Texture: Upper side of leaflet: Glossy and smooth. Under side of leaflet: Matte and smooth. Color, mature foliage: Upper Leaf Surface: Green Group 137A. Lower Leaf Surface: Green Group 138B. Color, juvenile foliage: Upper Leaf Surface: Green Group 137A. Lower Leaf Surface: Green Group 138B.

*Stipules.*—Size: 10 mm long. 5 mm between the tips of the stipule. Main body of stipule 4 mm in width. Shape: Longitudinally flanged or winged along middle. Apex: pointed. Base: rounded. Stipule color: Green Group 137A. Margins: Serrated.

*Petiole.*—Length: 10 mm. Diameter: 1 mm. Petiole color: Yellow-Green Group 144A. Margins: Entire with few thorns.

*Petiole rachis.*—Length: 35 mm. Diameter: 1 mm. Color: Greyed-Purple Group 184A and Yellow-Green Group 144A. Margins: With prickles.

*Leaflets.*—Size: Average size of the terminal leaflet is 40 mm (l)×30 mm (w). Shape: Broadly ovate. Base: Obtuse. Apex: Acute Margins: Serrated. Texture: Thick and leathery.

Hips/seed formation: None observed.

Winter hardiness: To date, the variety has been grown successfully in Zone 5.

Disease resistance: Above average resistance to mildew, rust, and Black spot diseases under normal growing conditions.

I claim:

1. A new and distinct variety of rose plant characterized by the following combination of characteristics:

(a) Forms attractive, long lasting flowers;

(b) Exhibits upright to bushy growth habit;

(c) Propagates well using traditional methods, and;

(d) Exhibits very good resistance to disease under normal growing conditions, substantially as herein illustrated and described.

* * * * *

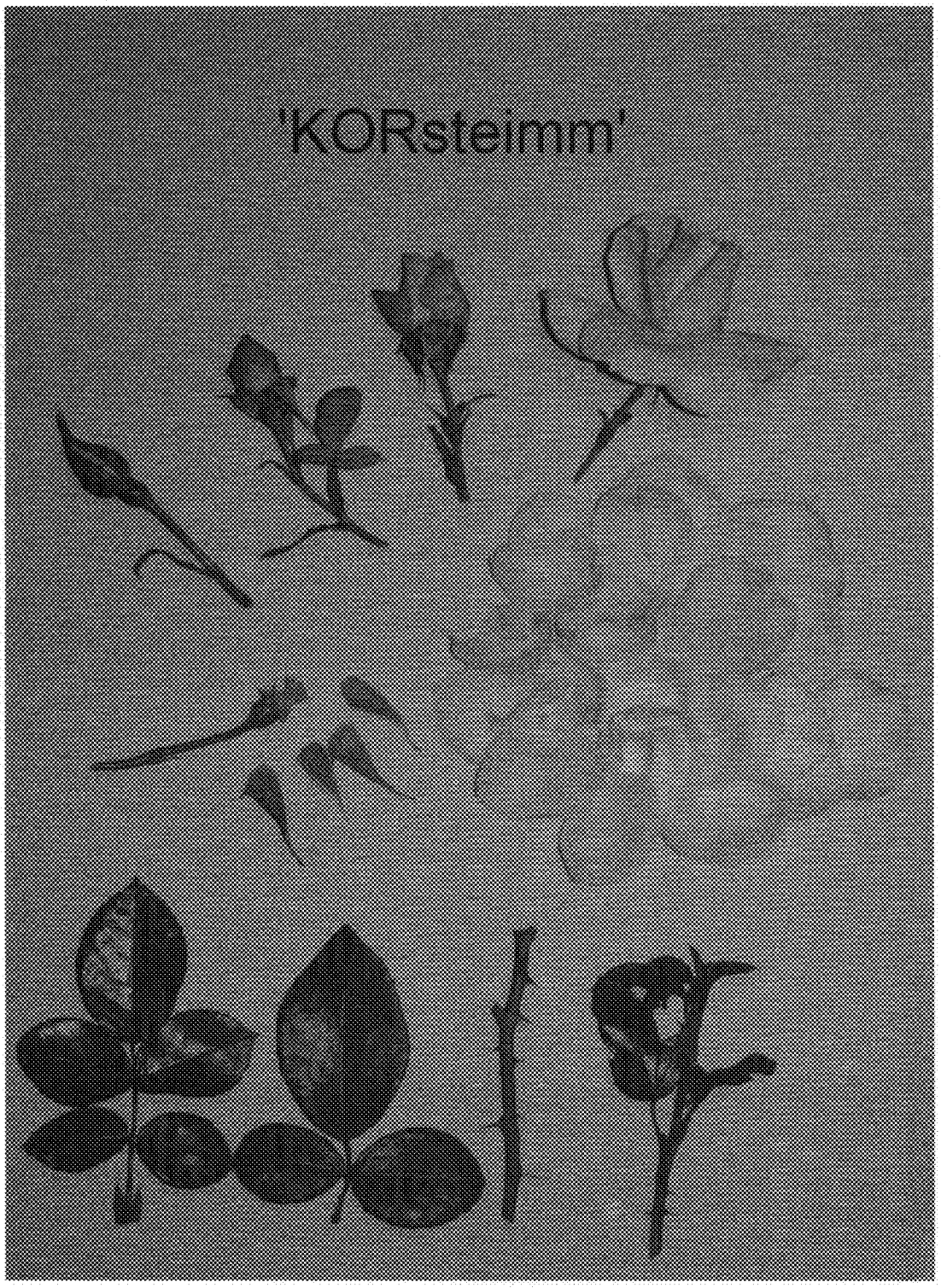
'KORsteimm'